United States Patent
Yoon et al.

(10) Patent No.: US 12,117,387 B2
(45) Date of Patent: Oct. 15, 2024

(54) BIOSENSOR, METHOD FOR MANUFACTURING THE SAME, AND ANALYSIS METHOD USING THE SAME

(71) Applicant: AJOU UNIVERSITY INDUSTRY-ACADEMIC COOPERATION FOUNDATION, Suwon-si (KR)

(72) Inventors: Hyun Chul Yoon, Seoul (KR); Jae-Ho Kim, Suwon-si (KR); Ka Ram Kim, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 18/007,348

(22) PCT Filed: Jul. 28, 2021

(86) PCT No.: PCT/KR2021/009754
§ 371 (c)(1),
(2) Date: Jan. 30, 2023

(87) PCT Pub. No.: WO2022/025604
PCT Pub. Date: Feb. 3, 2022

(65) Prior Publication Data
US 2024/0255410 A1    Aug. 1, 2024

(30) Foreign Application Priority Data

Jul. 30, 2020    (KR) .................. 10-2020-0095434

(51) Int. Cl.
*G01N 21/47* (2006.01)
*G01N 15/1434* (2024.01)
(Continued)

(52) U.S. Cl.
CPC ......... *G01N 15/1434* (2013.01); *G01N 21/51* (2013.01); *G01N 33/4833* (2013.01)

(58) Field of Classification Search
CPC ........ G01N 21/47; G01N 21/55; G01N 21/51; G01N 2021/516; G01N 2021/551;
(Continued)

(56) References Cited

U.S. PATENT DOCUMENTS 8,765,391 B2 * 7/2014 Zaugg .................. G01N 33/491
436/538
10,156,510 B2 * 12/2018 Tabata ................... G01N 21/05
(Continued)

FOREIGN PATENT DOCUMENTS

JP    2019-022536 A    2/2019
KR    10-1398764 B1    5/2014
(Continued)

OTHER PUBLICATIONS

International Search Report of PCT/KR2021/009754 dated Nov. 1, 2021 [PCT/ISA/210].

*Primary Examiner* — John R Lee
(74) *Attorney, Agent, or Firm* — Sughrue Mion, PLLC

(57) ABSTRACT

The present invention provides a cell measurement device and method in which retroreflective particles are introduced to measure cells, and thus, an optical signal is obtained without fixing of life activity of cells and performing a separate staining process. An example of the use of retroreflection-based cytometry is evaluation of cell migration. The cells capture the retroreflective particles during cell migration or growth, and migrate in a state that the particles are captured in the cell or bind to the cells. The migrated cells are observed in a form of bright dots inside the cells under irradiation of white light as a non-spectroscopic light source to the cells in the retroreflective optical system. The number of bright spots is counted, and thus, the number of cells and (Continued)

the presence thereof thus can be easily measured based on an image.

13 Claims, 5 Drawing Sheets

(51) Int. Cl.
*G01N 21/51* (2006.01)
*G01N 33/483* (2006.01)

(58) Field of Classification Search
CPC .. G01N 33/53; G01N 33/543; G01N 33/4833;
G01N 33/48; G01N 33/48735; G01N
33/48778; G01N 35/08; G01N 15/1434;
C12M 1/34; G02B 21/00; G02B 21/04
See application file for complete search history.

(56) References Cited

U.S. PATENT DOCUMENTS

| | | | |
|---|---|---|---|
| 10,175,159 B2* | 1/2019 | Wagner | G01N 15/1484 |
| 10,261,012 B2* | 4/2019 | Wagner | G01N 33/487 |
| 10,859,570 B2* | 12/2020 | Choi | G01N 33/54326 |
| 2008/0032324 A1* | 2/2008 | Walt | G01N 21/6458 |
| | | | 435/287.1 |
| 2012/0122084 A1* | 5/2012 | Wagner | G01N 15/14 |
| | | | 435/6.1 |
| 2016/0209409 A1* | 7/2016 | Choi | G01N 33/54326 |
| 2018/0038854 A1* | 2/2018 | Choi | B03C 1/01 |
| 2018/0371529 A1* | 12/2018 | Yoon | G01N 33/54373 |
| 2019/0154671 A1* | 5/2019 | Van Roosmalen | G01N 33/74 |
| 2019/0285625 A1* | 9/2019 | Kim | G01N 33/54386 |
| 2022/0371014 A1* | 11/2022 | Ryu | G01N 33/563 |
| 2023/0213507 A1* | 7/2023 | Yoon | G01N 33/533 |
| | | | 436/501 |

FOREIGN PATENT DOCUMENTS

| | | |
|---|---|---|
| KR | 10-1608942 B1 | 4/2016 |
| KR | 10-2017-0075221 A | 7/2017 |
| KR | 10-2019-0108005 A | 9/2019 |

* cited by examiner

BIOSENSOR, METHOD FOR MANUFACTURING THE SAME, AND ANALYSIS METHOD USING THE SAME

FIELD

The present disclosure relates to a biosensor, a method for manufacturing the same, and an analysis method using the same. More specifically, the present disclosure relates to a combination of a Boyden chamber, a non-spectroscopic white light source, and retroreflective particles that reflect lights from the light source at a strong signal level to perform cell migration and cell invasion analysis, a method for manufacturing the same, and an analysis method using the same.

DESCRIPTION OF RELATED ART

In conventional methods for performing optical quantitative and/or qualitative analysis of biological analyte, including immunological and molecular beacons, a signal intensity detection method of a signal label that emits fluorescence or light emission is applied to a reaction on a molecular basis. In this type of analysis method, optimization is performed in consideration of signal intensity and stability according to the type of the signal label. Along with the development of a new signal label, an optical analysis method optimized for the new signal label has also been developed. A form of the signal label may include an organic compound, metal complex compound, a particle carrying the same thereon, a quantum dot, green fluorescent protein (GFP), etc. The signal label is used in various ways according to requirements of each analysis goal depending on characteristics such as intensity, stability, duration, a form of a light-emitting spectrum, etc.

The signal label is also actively applied to the field of cell imaging and observation technology. Designing an organic fluorescent molecule targeting an organelle inside a cell or a specific material present in a cell, obtaining a fluorescence signal therefrom, and imaging the same is treated as a routine in the academic world for cells. However, the organic fluorescent molecule is often used as a label for a specific target within the cell structure. It is generally considered a more common test method to perform staining to distinguish the cells from a substrate. For example, chromophores or fluorescent materials that stain the nucleus or cytoplasm are used to label the cells and count the number of cells per unit area. The user counts the number of cells. However, the image is created and then a PC software is used to count the number of cells based on the image. In this process, additional life activities of cells are not required. Thus, in general, a fixing solution capable of stopping life activities of the cells and fixing morphological characteristics of the cells is used. Representative materials thereof may include various materials such as formaldehyde, paraformaldehyde, glutaraldehyde, methanol, and ethanol. The cell fixation process is an essential process before performing a staining process with chromophores or fluorophores.

In the Boyden chamber assay, which is one of the methods including the cell fixation process and the staining process, a structure based on a Boyden chamber in which a cylindrical cell culture well is bisected by a thin pore membrane into upper and lower chambers is used. Cells are injected into the upper chamber of the structure, and the culture medium including a substance that stimulates the cells in the upper chamber so as to activate migration of the cells is injected into the lower chamber. The assay counts the number of cells that migrate through the pore membrane and evaluates the function of the cells or the introduced migration-activating material, based on the counted number. In addition, a method of wound healing assay that physically made scratches the single-layered growing cell and evaluates the quickness of closure of the scratch area, a method of quantifying the number of flocked cells stimulated by continuous exposure to the migration-inducing material in the microfluidic chip has been developed and are being used up to now. In the Boyden chamber analysis method, which is the most traditional and still widely used, it is necessary to identify how many cells have migrated to the opposite side of the pore membrane to which the cells are attached. To this end, conventionally, after physically removing initially cultured cells using a cotton swab, the cells migrated onto the face are fixed, and are stained with a chromophore, and the number of cells is counted under a microscope.

The Boyden chamber assay may evaluate the migration performance of cells in a relatively simple and clear way, and thus is still used today. Numerous kits for the Boyden chamber assay have been commercialized. The most easily accessible kits, an insert-type supported simple well called a transwell is constructed in a common well plate, and a membrane is installed as a bottom of the transwell. The cells injected into the transwell are initially present only on a top face of the membrane. When the transwell is coupled to the well plate such that cells come into contact with the chemoattractant, the cells migrate to the opposite side of the membrane to the top face thereof. As a result, the migrated cells are fixed and stained, and the number of cells is measured. Researchers are using the above method.

However, in the evaluation of cell migration performance using the Boyden chamber assay, after a specified migration time has elapsed, the cells are fixed and stained, and identified through a microscope to measure the number of migrated cells. Thus, before the migration time has elapsed, it is impossible to monitor whether the cells migrate or not, as well as to identify the quantitative results thereof. Further, the results may be identified only at the end of the analysis. Thus, meaningless condition search experiments must be accompanied in the initial phase of experimental design. The fixation and staining processes of the migrated cells are mandatorily introduced because the distinction between the upper and lower surfaces is limited as a basis of the membrane, that is, the pore membrane in the transwell structure. For example, the thin pore membrane is disposed between the cells that migrated to the opposite side of the pore membrane and the cells that are initially introduced into the transwell. Thus, in order that cells that have migrated through the pore membrane during migration of the cells are clearly distinguished, the chromophore or fluorophore staining procedure should be performed and then cell counts should be observed. In order to solve these limitations, a method has been developed to bind the optical label to a position inside/outside the cell, and then count the cells that have migrated through the pore membrane and into the lower chamber.

In the optical phenomenon of fluorescence, fluorescent dyes that are excited by a light source and emit light of a wavelength may be stable by themselves. However, quenching thereof due to water molecules, and other electron transfer materials continuously exposed thereto between reactions, and self-quenching between fluorescent materials may occur. Further, photobleaching by excitation light having an intensity equal or greater than a certain intensity is also likely to be induced. For this reason, numerous trials and errors are required to select a fluorescent material for stable signal detection. Therefore, fluorescence signal labels based on organic/inorganic molecular groups should be optimized to optical equipment specifications, including light leakage and optical filtering according to the provided excitation light and emission wavelength. In addition, in the image detection method of biological tissues such as cells, the use of most organic/inorganic fluorescent molecules is avoided. This is because the excitation light wavelength of the molecular group is close to 400 nm in most cases, and the excitation wavelength that penetrates the cell is in an ultraviolet light region that may cause denaturation and destruction of proteins including genetic materials (DNA, RNA) inside the nucleus. Thus, it is difficult to obtain research results on living cell activity unless the purpose thereof is to chemically fix the activity of the cell. Regarding a detailed example of conventional fluorescence and optical cell analysis techniques including the above limitations, first, there is an observation method using intracellular green fluorescence protein or luciferase. In this scheme, a viral vector is introduced (transfection) to express the green fluorescence protein or luciferase in cells, and thus a variable that can affect the activity of the actual cell itself is added. Second, the case of using a quantum dot has problems that in the intracellular environment lower the quantum efficiency, and the cytotoxicity caused by the heavy metal constituting the quantum dot must be introduced into the cell. Thus, using the quantum dot was limited in cell observation. In order to detect a fluorescence signal from fluorescent dyes, it is necessary to perform the separation between the irradiated excitation light and the fluorescence signal derived from the fluorescent dye in response to the irradiated excitation light. Therefore, a separate emission filter is essential. Further, for sensitive detection of the fluorescence signal, expensive light receiving equipment such as photomultiplier tube (PMT) is essential. In addition, very sophisticated arrangement and assembly between these optical parts are required. This acts as a limiting factor in the implementation of equipment for the purpose of performing cell observation for a more general purpose.

DISCLOSURE

Technical Purpose

An optical analysis method of a biological substance is widely used not only to analyze the presence or absence of a target molecule, but also to observe life phenomena appearing in a biological specimen. Thus, simplification of an optical analysis device of the biological substance is essential for general-purpose use.

Therefore, one purpose of the present disclosure is to provide a methodology in which the chromophore and fluorophore labels used in conventional cell imaging and observation are avoided, and cell migration that could only be identified at the end time of cell migration ability evaluation can be identified in real time, and a device for observing the cell migration is simplified. To this end, in this methodology, retroreflective particles bind to a position inside/outside the cytoplasm, and cells which have migrated under influence of a chemoattractant are observed using a retroreflective optical system. Thus, the migration of cells may be observed in real time and a retroreflective signal may be easily obtained without using a complicated optical system.

Another purpose of the present disclosure is to provide a biosensor to which the above methodology is applied, a method for manufacturing the biosensor, and an analysis method using the same.

Technical Solution

In the conventional scheme, in order to perform quantitative counting of migrating cells, cell vital activities are fixed and the cells are subjected to a dye staining process using a color-developing/fluorescent material, and the cell migration is observed under a microscope. However, in accordance with the present disclosure, retroreflective particles are used as cell labels, such that the vital activity of migrating or infiltrating cells is not fixed, and at the same time, cell behavior is observed in real time at a desired time point while the staining or color development is not performed. To this end, in accordance with the present disclosure, retroreflective particles are mixed with an extracellular matrix (ECM), and the mixture is coated on a membrane with pores constituting the bottom of the transwell. The chemoattractant flows through the coating layer so as to activate the migration of the cells in the transwell. While the cells migrate through the coating layer and the pores, the retroreflective Janus particles (RJP) in the coating layer are injected into the cytoplasm. While the RJP is introduced into the cell cytoplasm, the cells migrate through the membrane as the bottom of the transwell, and then migrates to a well of a lower structure supporting the transwell and adhere to the bottom surface of the well of the lower structure. Then, a retroreflective signal based on retroreflective particles present inside the cell may be obtained through the retroreflective optical system.

Technical Effect

According to the present disclosure, the retroreflective particles that are contained in cells or bind to the cells is not subjected to a conventional chromophore/fluorophore staining process. Thus, the cells are not separately fixed or an experimental process is not configured for the conventional chromophore/fluorophore staining process. Rather, in the process of the cell migration in response to the chemoattractant, the cells may naturally intake or capture retroreflective particles inside the cells or the retroreflective particles may bind to the cells. Thus, the label may be modified on the cell in a state that does not interfere with the life activity of the cells, and the migration of the living cells may be monitored in real time. Further, even after the cell migration, the particles be present in or on the cells. The well plate containing the cells therein is installed on the retroreflective optical system. Thus, the retroreflective signal from the retroreflective particles may be easily obtained in a form of an image using an optical microscope of the retroreflective optical system. The image may be analyzed using software to easily count the retroreflective particles. Thus, quantitative analysis of the cells to be observed may be performed.

Further, an extremely simple light source device is added to a general optical microscope so as to induce the retroreflection. The optical sensor according to the present disclosure may be applied to a conventional commercialized system in a non-modified manner. A retroreflective particle layer may be coated on a conventional and commercially available commercial kit to achieve the same effect as the above-described effect. Thus, the biosensor according to the present disclosure has very wide application. Further, the behavior of the cells appearing in the cell migration ability evaluation test may be observed over time. Thus, a very easy observation device and method that does not force an experimenter who is non-familiar with an experiment to perform optimization may be realized.

BRIEF DESCRIPTION OF DRAWINGS

In FIG. 6, ① shows a bright field of the microscope, ② shows a retroreflective optical setting using side white light after turning off a bright field light source of the microscope, ③ shows a microscope image (100 magnification) obtained through the bright field, and ④ shows a microscope image (100 magnification) obtained through the retroreflective setting.

DETAILED DESCRIPTIONS

Figure 1:
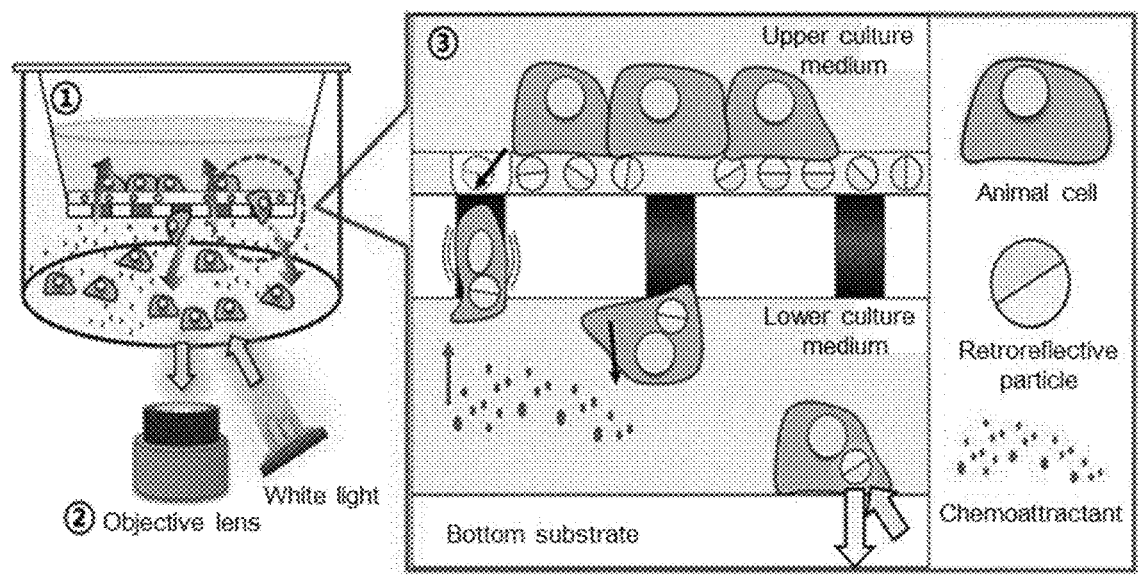
FIG. 1 is a schematic diagram for illustrating a biosensor according to an embodiment of the present disclosure.

Hereinafter, an embodiment of the present disclosure will be described in detail with reference to the accompanying drawings. The present disclosure may be variously modified and may take many forms. Thus, specific embodiments will be illustrated in the drawings and described in detail herein. However, the specific embodiments are not intended to limit the present disclosure thereto. It should be understood that all changes, equivalents thereto, or substitutes therewith are included in a scope and spirit of the present disclosure. In describing the drawing, similar reference numerals are used for similar components.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Analysis of cell migration performance is an important indicator for diagnosing diseases including cancer. Specific examples thereof include analysis of cancer cell metastasis ability or immunogenic activity of immune cells. The change in the migration performance of the observed target cell is greatly involved in the growth change of the cell, and may be used as an index for diagnosing diseases.

Representative cell migration performance evaluations are largely classified into following two: cell migration assay which identifies whether cells exhibit chemotaxis to chemoattractant and thus migrate to a specific section; and cell invasion assay which identifies the ability of the cells to penetrate a specific tissue.

The mechanical part and experimental procedures for performing the above two analysis methods include various schemes such as a traditional Boyden chamber, wound healing assay, or evaluation of migration/invasion performance using a microfluidic chip platform, etc. However, in accordance with the present disclosure, a retroreflection-based cytometry methodology based on the Boyden chamber analysis method is introduced.

Biosensor

FIG. 1 is a schematic diagram for illustrating a biosensor according to an embodiment of the present disclosure. Referring to FIG. 1, the biosensor according to an embodiment of the present disclosure may include a Boyden chamber including a transwell structure and a well of a well plate supporting the transwell structure, a light-emitter, and a light-receiver.

Hereinafter, the transwell structure of the Boyden chamber is referred to as "a first chamber" and the well of the well plate is referred to as "a second chamber".

The first chamber is a structure having an inner space capable of containing therein cells to be observed. The first chamber may include a bottom having a membrane structure including a plurality of micropores extending through the bottom so that the cells can migrate from an inside of the first chamber to an outside out of the first chamber; a sidewall extending upward from the bottom such that the inner space is defined by the sidewall and the bottom; and a coating layer formed on the bottom and containing retroreflective particles therein.

The bottom of the membrane structure of the first chamber may be made of a polymer material. For example, the membrane may be made of a material such as polystyrene, polyethylene, polycarbonate, or the like. The micropores may be holes through which the cells can migrate, and a size of the micropore is not particularly limited as long as the cell can migrate out of the first chamber through the micropore. For example, the micropore may have a size of about 3 to 10 μm. In one embodiment, the size of the micropore may be about 8 μm.

The coating layer may include a gel-type matrix and the retroreflective particles dispersed in the matrix. The matrix may be made of a biocompatible material that does not exhibit cytotoxicity. For example, the matrix may include collagen types 1 to 4, polycaprolactone, gelatin, and poly(lactic-co-glycolic acid), hyaluronic acid, and an extracellular matrix (ECM). In one embodiment, the matrix may be made of an extracellular matrix (ECM).

In one embodiment, in order that the cells can migrate only through a specific area to provide convenience in observing cell migration, the coating layer may include a first area through which the cells can migrate and a second area through which the cells cannot migrate. In this case, the retroreflective particles may be present only in the first area. For example, the first area may be located in a central portion of the bottom, and the second area may be located to surround the first area.

In one embodiment, the first area and the second area may be formed by adjusting a concentration of the biocompatible material constituting the matrix. For example, the first area may be formed using a solution containing the biocompatible material at a low concentration and may be present in a gel form. The second area may be formed using a solution containing the biocompatible material at a high concentration, and may be present in a high density gel or in a solid state.

The retroreflective particle causes a retroreflective phenomenon in which the particle reflects light incident thereto toward the light source, and can induce the retroreflective phenomenon of incident light with a wavelength smaller than a particle size. Further, the retroreflective particle may easily induce the retroreflection of non-spectroscopic white light with various wavelengths of visible light. The retroreflective particle may induce the retroreflection when the retroreflective particle is located on a surface of a cell or inside the cell.

In one embodiment, the retroreflective particle may include a transparent core particle and a reflective layer covering a portion of the core particle so as to induce total reflection of incident light. In one example, the retroreflective particle may further include the first bio-cognitive material that is modified on the core particle or the reflective layer and can selectively bind to a cell to be observed.

The core particle may have a spherical shape. In the present disclosure, the 'spherical shape' is defined to include not only a full sphere in which radii from a center to all points on a surface thereof are equal to each other, but also a substantial sphere in which a difference between a maximum radius and a minimum radius is about 10% or smaller of the maximum radius. The core particle may have an average diameter in a range of about 500 nm to 5 μm, for example, about 700 nm to 1 μm, in consideration of the binding ability with the cell to be observed, a relationship between the size of a wavelength of light irradiated from the light source, and sedimentation ability in a detection solution.

In one embodiment, the core particle may be made of a transparent material capable of transmitting incident light therethrough. For example, the core particle may be made of a transparent oxide or a transparent polymer material. The transparent oxide may include, for example, silica, glass, and the like, and the transparent polymer material may include, for example, polystyrene, poly(methyl methacrylate), and the like.

The first bio-cognitive material may be made of a material capable of selectively binding to a cell to be observed, and a type thereof may be changed according to a type of the cell to be observed. For example, the first bio-cognitive material may be an antibody or a ligand functional group that exhibits a specific reaction with a surface protein. In one embodiment, the first bio-cognitive material may be directly or indirectly bonded to an exposed portion of a surface of the core particle.

In one example, the second chamber may include an inner space capable of containing cells migrating from the first chamber, and may be combined with the first chamber so as to support the first chamber. In a state in which the first chamber and the second chamber are coupled to each other, at least a portion, for example, the bottom of the first chamber may be received in the inner space of the second chamber.

The second chamber may include a bottom disposed to be spaced apart from the bottom of the first chamber and a sidewall extending upward from the bottom such that the inner space is defined by the sidewall and the bottom. In one embodiment, the bottom of the second chamber may be made of a light-transmitting material so that the bottom transmits light emitted from the light-emitter therethrough. Thus, a retroreflective signal can be obtained. For example, the bottom of the second chamber may be made of a transparent polymer material such as poly(methyl methacrylate) (PMMA), polycarbonate (PC), or polystyrene (PS). However, the present disclosure is not necessarily limited thereto. Any material may be used as a material of the bottom of the second chamber as long as the material is capable of transmitting light therethrough.

In one embodiment, a culture medium and the cells may be received in the inner space of the first chamber, and the culture medium and chemoattractant may be received in the inner space of the second chamber. The culture medium may be applied without limitation as long as it does not inhibit the growth of the cells. In addition, the chemoattractant activates the migration ability of the cells. Any material that may activate the migration ability of the cells may be applied as the chemoattractant without limitation. A type of the chemoattractant may be changed depending on a type of the cell. For example, the chemoattractant may include monocytechemoattractant protein-1 (MCP-1) that is effective on macrophages.

In one embodiment, in a state in which the first chamber and the second chamber are coupled to each other, the chemoattractant can diffuse into the first chamber to activate the migration ability of the cells in the first chamber. Thus, the cells received in the inner space of the first chamber can migrate to the inner space of the second chamber through the bottom of the membrane structure of the first chamber. At this time, the cells migrate through the coating layer containing the retroreflective particles therein. In this regard, while the cell migrates through the coating layer, the cell may contain therein the retroreflective particle therein via an uptake or phagocytosis action, or the retroreflective particle may be bound to a surface of the cell via a selective reaction of the cell with the first bio-cognitive material on the surface of the retroreflective particle. In this state, the cell can migrate to the inner space of the second chamber. The cells migrating to the inner space of the second chamber may be attached to a surface of the bottom of the second chamber.

The light-emitter and the light-receiver may be disposed below the second chamber. The light-emitter may irradiate light toward the bottom of the second chamber. The light-receiver may receive light retroreflected from the retroreflective particle contained in the cell attached to the bottom of the second chamber or the retroreflective particle coupled to the surface of the cell, and then may generate quantitative information about the retroreflective particles.

In one embodiment, a light source of the light-emitter is not particularly limited, and may include, for example, a white LED generating white light. The light-receiver may include an optical microscope capable of generating an image of the retroreflected light and an image processing device capable of counting the number of retroreflective particles based on an analyzing result of the image generated by the optical microscope. A configuration of the light-receiver is not particularly limited as long as it generates the image of the retroreflected light and counts the number of retroreflective particles from the image. In one example, the light-receiver may analyze change in the number of retroreflective particles in real time to analyze cell migration information in real time.

According to the biosensor of the present disclosure, while the cell to be observed migrates from the inner space of the first chamber to the inner space of the second chamber, the cell to be observed uptakes and receives therein the retroreflective particle or selectively reacts with the retroreflective particle and binds thereto. Therefore, light may be irradiated onto the retroreflective particles located in the inner space of the second chamber and then the migration of the cells may be detected in real time based on an analyzing result of the retroreflected light.

Method for Manufacturing Biosensor

Figure 2:
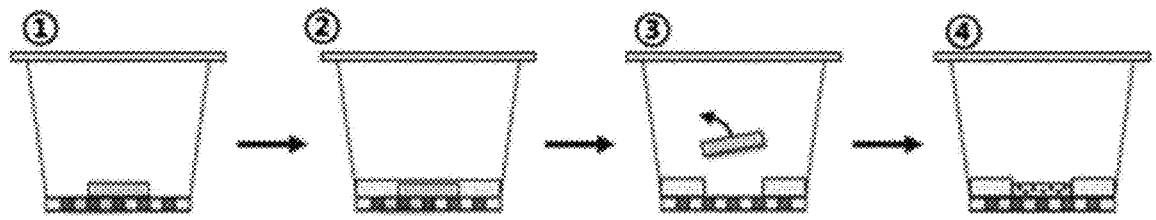
FIG. 2 is a diagram for illustrating a method for manufacturing a biosensor according to an embodiment of the present disclosure.

FIG. 2 is a diagram for illustrating a method for manufacturing a biosensor according to an embodiment of the present disclosure. In particular, FIG. 2 illustrates a method for forming a coating layer that may induce cell migration only through a specific area of the bottom of the first chamber. For convenience of description, hereinafter, a portion of the coating layer through which the cells can migrate is referred to as a permeable area, and a portion thereof through which the cells cannot migrate is referred to as a blocking area.

Referring to FIG. 2, in order to form the coating layer having the permeable area and the blocking area, first, as shown in ① and ② of FIG. 2, a disk is attached to a portion of the bottom face of the first chamber corresponding to the permeable area, and then a first composition prepared by mixing the biocompatible material at a high concentration with the culture medium is applied to a portion of the bottom face thereof not covered with the disk. Thus, the blocking area may be formed. In this regard, the disk may have a structure of a circular plate having an area smaller than that of the bottom face of the first chamber. A material of the disk is not particularly limited, but is preferably embodied as a material that may be temporarily attached to the bottom face of the first chamber.

In one embodiment, in order to form the blocking area, the first solution may be applied to the portion of the bottom face of the first chamber not covered with the disk, and then, bubbles may be removed therefrom at about 2 to 6° C. for about 10 to 14 hours. Subsequently, the applied first composition may be converted to a gel at a temperature of about 35 to 40° C. for about 1 to 3 hours.

Subsequently, as shown in ③ and ④ of FIG. 2, the disk may be removed from the bottom face of the first chamber. Then, a second composition prepared by mixing the biocompatible material at a low concentration and the retroreflective particles with the culture medium may be applied to an area from which the disk has been removed. Thus, the permeable area may be formed.

In one embodiment, in order to form the permeable area, the second composition may be prepared by mixing the biocompatible material, the culture medium, and a retroreflective particle aqueous solution in a volume ratio of about 25 to 35:850 to 900:90 to 110. The second composition is applied to the area from which the disk has been removed, and then air bubbles may be removed therefrom at about 2 to 6° C. for about 10 to 14 hours. Subsequently, the applied second composition may be converted to a gel at a temperature of about 35 to 40° C. for about 1 to 3 hours.

In one embodiment, the biocompatible material may include the ECM (extracellular matrix). ECM is widely used in general cell invasion analysis. Coating using ECM mimics morphological characteristics of other cell tissues. Coating using the ECM may allow a desired material to be coated in a gel form while not exhibiting cytotoxicity.

In the second composition, the biocompatible material may have a diluted concentration. For example, the biocompatible material may have a concentration diluted by about 10 to 30 times. When the coating layer is formed using a high-concentration biocompatible material, it may be very difficult for the cells to migrate through the coating layer. Therefore, preferably, the biocompatible material may have a concentration diluted by about 10 to 30 times.

The culture medium is capable of culturing a cell to be observed. Different types of the culture medium may be used depending on different types of the cell. In one embodiment, the culture medium may be DMEM (Dulbeccos Modified Eagles Medium).

In one embodiment, after forming the coating layer including the permeable area and the blocking area on the bottom face of the first chamber, additional washing and drying processes may be performed thereto. In one embodiment, the washing may be performed using a phosphate buffer solution and ultrapure water, and the drying may be performed at room temperature.

Analysis Method Using Biosensor

Figure 3A:
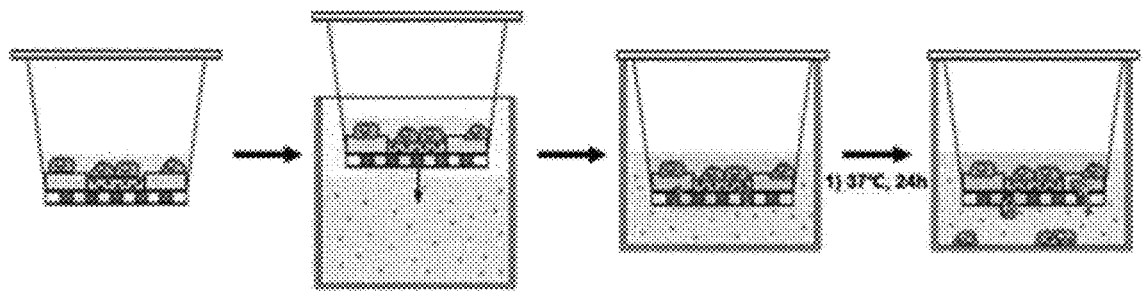
FIG. 3A and FIG. 3B are drawings for illustrating an analysis method using the biosensor as shown in FIG. 1.
Figure 3B:
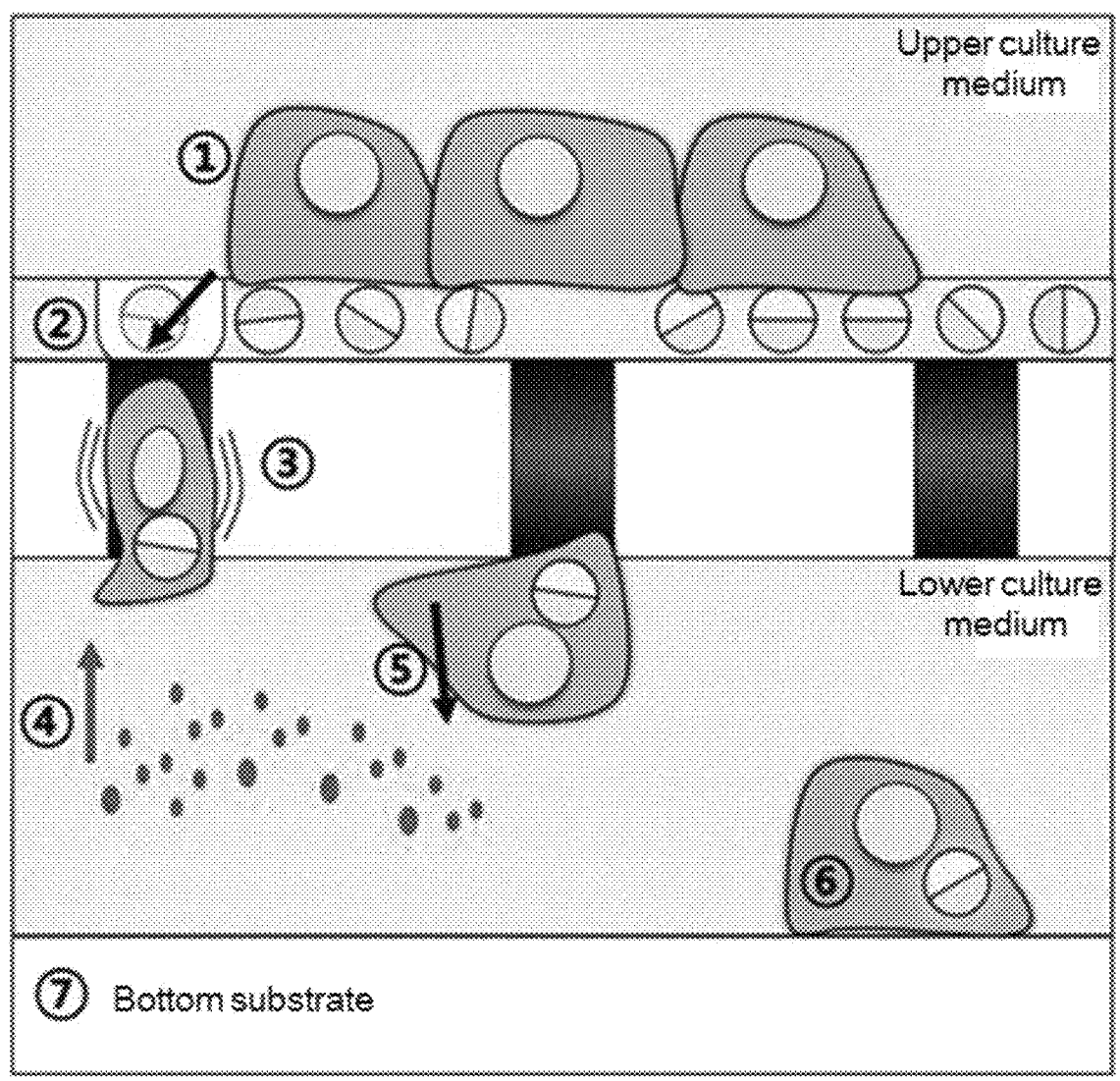

FIG. 3A and FIG. 3B are diagrams for illustrating an analysis method using the biosensor according to an embodiment of the present disclosure as shown in FIG. 1.

Referring to FIG. 3A and FIG. 3B together with FIG. 1, first, in order to evaluate cell migration performance, the cells together with a first culture medium may be put into the inner space of the first chamber. Thus, the cells may be cultured therein.

The first culture medium may include a serum-free culture medium such as fetal bovine serum (FBS) in order to increase an effect of the chemoattractant rather than a complete culture medium for cell growth that is generally used. The first culture medium may maximize the effect of the chemoattractant. This may be because a large amount of several chemokine factors including growth factors for cell growth are contained in the serum.

A cell density may vary depending on a cell type. In one embodiment, the density of the cells may be about $5 \times 10^5$ cells/mL based on a 12 well plate.

Subsequently, the chemoattractant and a second culture medium may be input into the inner space of the second chamber. Then, the first chamber containing the cultured cells therein may be coupled to the second chamber such that at least the bottom of the first chamber may be immersed in the second culture medium contained in the inner space of the second chamber.

When, in this way, at least the bottom of the first chamber is kept submerged in the second culture medium received in the inner space of the second chamber, the chemoattractant can diffuse into the inner space of the first chamber. Thus, the migration ability of the cells can be activated by the diffused chemoattractant. Thus, the cells can migrate from the inner space of the first chamber to the inner space of the second chamber. At this time, the cells can migrate through the coating layer and then can migrate to the second chamber through the pores formed in the bottom of the first chamber. While the cells migrate through the coating layer, the retroreflective particles inside the coating layer can migrate into the cells or may be bonded to the cells. Thus, the retroreflective particles together with the cells can migrate to the second chamber. For example, while the activated cells migrate through the coating layer, the cells may capture the retroreflective particles into the cytoplasm via the uptake or phagocytosis in case of immune cells. The cells that have migrated into the inner space of the second chamber in a state in which the retroreflective particles are captured therein may be attached to the bottom surface of the second chamber.

The migration of the cells may be performed for about 6 to 48 hours. For example, the migration of the cells may be performed for about 20 to 28 hours. Further, the migration of the cells may be performed at a temperature of about 35 to 38° C. and under an about 3 to 7% carbon dioxide condition.

Subsequently, light may be irradiated on the cells attached to the second chamber. Thus, retroreflection of the light from retroreflective particles bound to the cells or trapped inside the cells may be induced.

In one embodiment, the light irradiated to the cells may be white light. The light may be irradiated from a position under the second chamber and may be incident through the bottom of the second chamber. The light retroreflected from the retroreflective particles may travel through the bottom of the second chamber and reach the light-receiver.

Then, the light-receiver may convert an optical signal of the light retroreflected from the retroreflective particle into an image, and may perform quantitative analysis of the retroreflective particles based on the image. In this regard, the light-receiver may include the optical microscope, and may analyze the migration performance of the cells based on the quantitative analysis result of the retroreflective particles.

In one embodiment, the light-emitter and the light-receiver may be implemented using the white LED and a general optical microscope, respectively. In one example, in the optical image generated from the light-receiver, a retroreflective signal corresponding to the light reflected from the retroreflective particles present inside/outside the cell may appear in a form of a shining dot. The number of these shining dots may be counted using an image analysis device. Thus, the light-receiver may quantitatively analyze the number of the cells which have migrated from the first chamber to the second chamber, based on the counted number. In one example, in order to count the number of the shining dots in the optical image, a background noise level of an original image may be lowered, and a RGB value of a pixel may be converted to 8-bits. Then, an algorithm that calculates a difference between brightness data of the dot resulting from retroreflective particle in the cell and the background, and recognizes only pixels having the difference larger than or equal to a predefined value as dots resulting from the retroreflective particles, and calculates the number of the recognized pixels may be introduced. Thus, the number of retroreflective signals may be measured.

In one example, the measurement of the retroreflective signal may be performed in a state in which the first chamber and the second chamber are coupled to each other, or may be performed in a state in which the second chamber is removed from the first chamber. For example, when the retroreflective signal is continuously measured in a state in which the first chamber and the second chamber are coupled to each other, the cell migration may be analyzed in real time.

According to the present disclosure, the retroreflection may be induced by adding a very simple light source device to a general optical microscope. Thus, the biosensor according to the present disclosure may be applied to a conventional system in a non-modified manner. Further, the behavior of the cells appearing in the cell migration ability evaluation test may be observed over time. Thus, a very simple observation device and method that does not force an experimenter who is non-familiar with an experiment to perform optimization may be realized. A retroreflective particle layer may be coated on a conventional and commercial kit to achieve the same effect as the above-described effect. Thus, the biosensor according to the present disclosure has very wide application.

Hereinafter, the present disclosure will be described in more detail via Specific Examples and Experimental Examples. However, Examples of the present disclosure are only some embodiments of the present disclosure. The scope of the present disclosure is limited to the following Examples.

The applicant of the present disclosure has developed a retroreflection-based cell observation principle and has implemented a novel cell migration performance evaluation methodology to which the retroreflection-based cell observation principle is applied. In the retroreflection-based cell observation principle and the novel cell migration performance evaluation methodology, an optical system of a complex configuration of an absorption phenomenon or fluorescence/light-emitting based analysis system representative of a signal acquisition strategy of conventional cell imaging technology is simplified, and at the same time, conventionally used labels for real-time cell monitoring, such as light absorbing materials, organic fluorescent dyes, and particles impregnated therewith are replaced with the retroreflective particles (retroreflective Janus particles, hereinafter sometimes referred to as RJP). In order to optically observe the microscopic behavior of cells, the cell sample is fixed using a reagent that stops life activities such as formaldehyde, methanol or glutaraldehyde, and then, organic fluorescent dyes, quantum dots, upconversion nanoparticles, or chromophores as labels for obtaining optical signals are injected into cells (dye staining). However, in accordance with the present disclosure, cell observation using the retroreflective observation method is developed such that the experimental procedure of the conventional cell immobilization and staining process is further simplified, and the principle of cell observation using the retroreflective phenomenon in the optical system, and an observation methodology using the principle are developed. We will verify use thereof in evaluating cell migration performance as follows.

EXAMPLES

Example 1

In Example 1 for the experimental example of the present disclosure, a biosensor manufactured according to an embodiment was used to perform the migration performance analysis of macrophages. In this experimental example, the RAW264.7 cell line was put into the upper transwell (the first chamber), and phagocytosis was induced on the retroreflective particles coated on the membrane of the transwell (the first chamber). Cell migration was analyzed based on retroreflective signals resulting from the cells migrating to the lower well (second chamber) under influence of the chemoattractant.

Experimental Example 1: Identification of Capturing Retroreflective Particle by Macrophage Phagocytosis, and Verification of Cytotoxicity In order to verify the cytotoxicity of retroreflective particles as a non-spectroscopic optical label for cytometry as newly introduced in accordance with the present disclosure, retroreflective particles of various concentrations were prepared and added to a culture medium, and the culture medium was administered to growing cells. Thus, the cytotoxicity of retroreflective particles was verified. The cells used in the examples were RAW264.7 cell line as a rat-derived macrophage cell line and was cultured in a well plate (the second chamber) at a density of $5 \times 10^5$ cells/mL for 6 hours. Then, the previous culture medium was replaced with complete culture medium (Dulbecco modified Eagle medium (DMEM) (10% fetal bovine serum, and 1% penicillin streptomycin (PS)) containing retroreflective particles therein and the cells were cultured therein for 24 hours. MTS (3-(4,5-dimethylthiazol-2-yl)-5-(3-carboxymethoxyphenyl)-2-(4-sulfophenyl)-2H-tetrazolium was input to the medium as a reagent allowing the cells growing normally to generate an absorbent material absorbing light of 490 nm. Cytotoxicity was measured by comparing the cell growth in the medium containing retroreflective particles therein and a cell growth of a control that was not treated with the retroreflective particles with each other. The results are as shown in FIG. 4.

Figure 4:
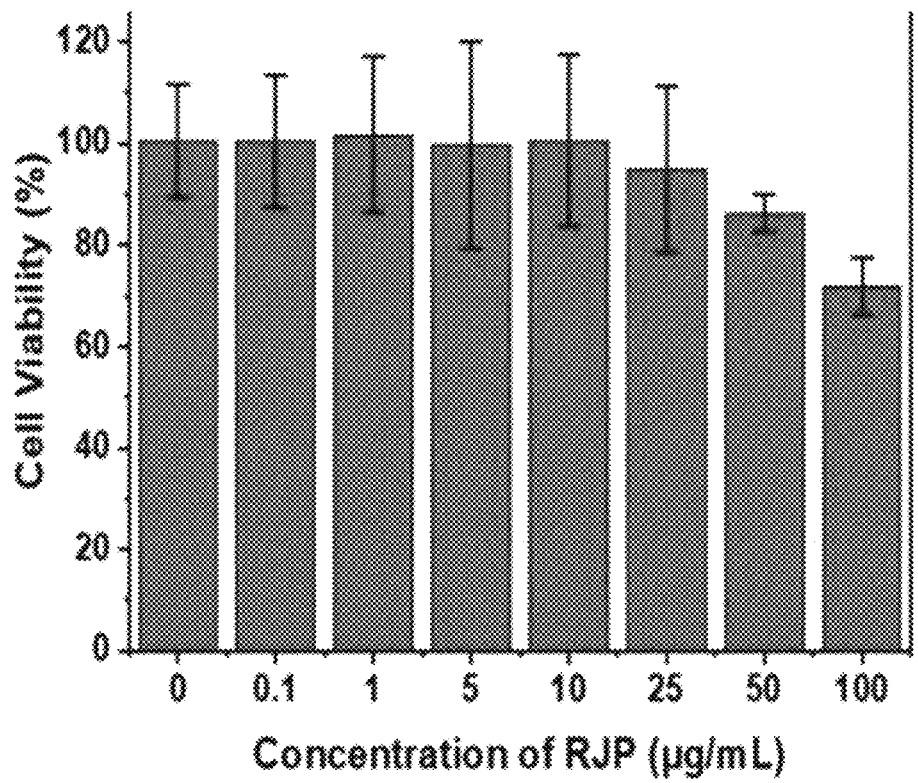
FIG. 4 is a diagram showing evaluation of cytotoxicity based on a retroreflective particle concentration to illustrate Experimental Example 1 of the present disclosure.

Referring to FIG. 4, it may be identified that the retroreflective particle concentration in the culture medium which exhibits a difference in cell growth activity of 5% or greater compared to the control is 25 ug/mL.

Thus, in the following experimental examples, the concentration of the retroreflective particles in the coating layer used in the present disclosure was designated as 10 ug/mL.

Experimental Example 2: Obtaining Retroreflective Signal from Retroreflective Particle Present in Cell In order to demonstrate the retroreflective signal detection of the retroreflection-based cytometry method developed in accordance with the present disclosure, an experiment was performed to evaluate whether or not a signal was observed under a microscope. The maximum value of the retroreflective particle concentration in a range that does not inhibit the cell growth as shown in Experimental Example 1 (FIG. 4) was 10 ug/mL. Thus, in this Experimental Example 2, the RAW264.7 cell line cultured in the well plate (the second chamber) was treated with the retroreflective particles at the above concentration 10 ug/mL. After 24 hours, the bright field image observed from the cells in the state in which the retroreflective particles were captured therein, and the retroreflective signal as obtained by irradiating a white light source provided on a side of the objective lens to the cells in the state in which the retroreflective particles were captured therein were measured in the same section. The results are as shown in FIG. 5.

Figure 5:
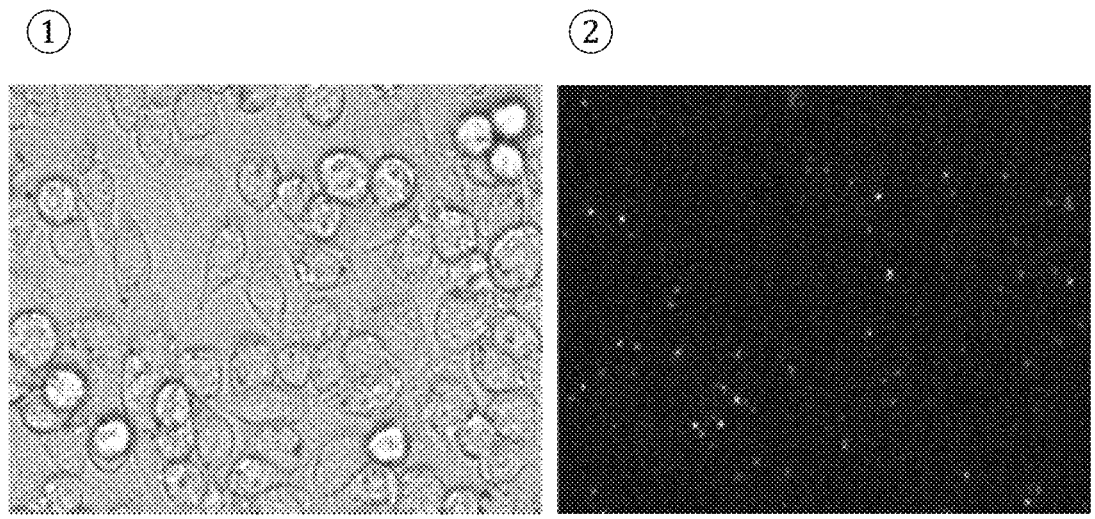
FIG. 5 is images showing cells capturing RJPs observed respectively through bright field and retroreflective settings for illustrating Experimental Example 2 of the present disclosure. ① in FIG. 5 is an image (magnification of 200) of a RAW 264.7 cell line capturing retroreflective particles observed through a bright field of an optical microscope. ② in FIG. 5 is a retroreflective signal image (200 magnification) of retroreflective particles obtained by irradiating a white light source to induce retroreflection.

Referring to FIG. 5, in the bright field image of ①, the retroreflective particles present inside the cells appeared as black dots. As shown in ②, in the image where the retroreflective signal was obtained by irradiating the side white light source to the cells while the bright field was removed, the particles that appeared as the black dots in the bright field image appeared in the form of bright dots. Thus, it may be identified that although the retroreflective particles are captured inside the cells, the cells themselves have little light interference, so that the retroreflective particle-based optical signals are captured by the objective lens of the microscope at high intensity. However, the orientation of the retroreflective particles at which the particles retroreflect the light is fixed. Thus, when the orientation of the retroreflective particles present in the cells is not correct stochastically, the retroreflective particles present in the cells may not reflect light under a retroreflective setting.

Experimental Example 3: Identification of Migration of Macrophages Capturing RJP Therein Using Retroreflective Observation Experimental Example 3 was conducted to verify that the RAW264.7 cell line cultured in the transwell (the first chamber) coated with the retroreflective particles migrated under influence of monocytechemoattractant protein-1 (MCP-1) as the chemoattractant present in the lower chamber (second chamber), and migrated to the bottom substate of the well plate (the second chamber). In this example, DMEM (Dulbeccos Modified Eagles Medium) was used as the serum-free culture medium in the upper chamber. The culture medium in the lower chamber was composed of 1 ng/ml MCP-1, 10% Fetal Bovine Serum (FBS), and 1% Penicillin streptomycin (PS) based on DMEM (Dulbeccos Modified Eagles Medium). After the first chamber and the second chamber were combined with each other, the cell migration time was specified for 24 hours to observe the cell migration, and the cell migration was observed while culturing the cells in a cell incubator. The results are as shown in FIG. 6.

Figure 6:
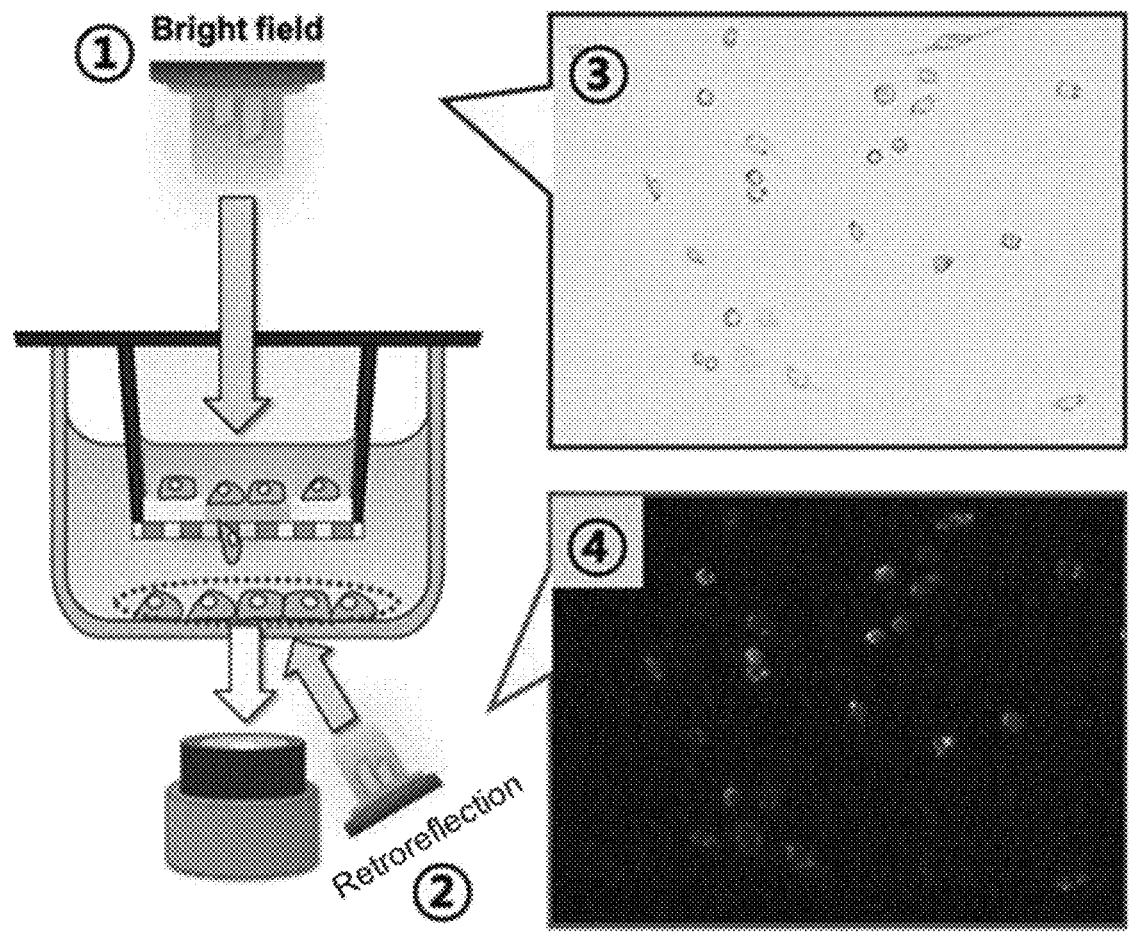
FIG. 6 is bright field and retroreflective signal images of cells migrated to a lower layer by chemoattractant for illustrating Experimental Example 3 of the present disclosure.

Referring to FIG. 6, the bright field image shown in ③ is an image of cells migrated to the bottom substrate of the well plate (the second chamber) and shows the appearance of the cells which have migrated through the coating layer including the retroreflective particles and the membrane structure (8 μm pore membrane) with pores of the transwell (the first chamber) and toward the bottom (bottom substrate) of the second chamber. Retroreflective particles appearing as the black dots are observed in each of the cell. When these particles are measured under the retroreflective optical setting, it may identified that bright dots be present in the cells as shown in ④. In this way, cell migration performance may be analyzed.

Experimental Example 4: Evaluation of Dependence of Macrophage Migration Performance on Chemoattractant Concentration In Experimental Example 4, an experiment was conducted to verify whether the novel developed retroreflection-based cytometry can be used for an evaluation of cell migration dependence on the concentration of the chemoattractant as used in general cell migration analysis. The MCP-1 introduced into the well plate (the second chamber) was added into the culture medium at a concentration of each of 0, 1, 10, and 100 ng/ml. The RAW264.7 cell line at a concentration of $5 \times 10^5$ cell/mL was cultured in the transwell (the first chamber). The transwell (the first chamber) was coupled to the well plate (the second chamber). The cells have migrated from the first chamber to the second chamber. As a result, as shown in FIG. 7, the increase in the number of cells that migrated for 24 hours in the concentration range of 0 ng/ml to 10 ng/ml of MCP-1 was observed with an optical microscope, and an image thereof is as shown in FIG. 7.

Figure 7:
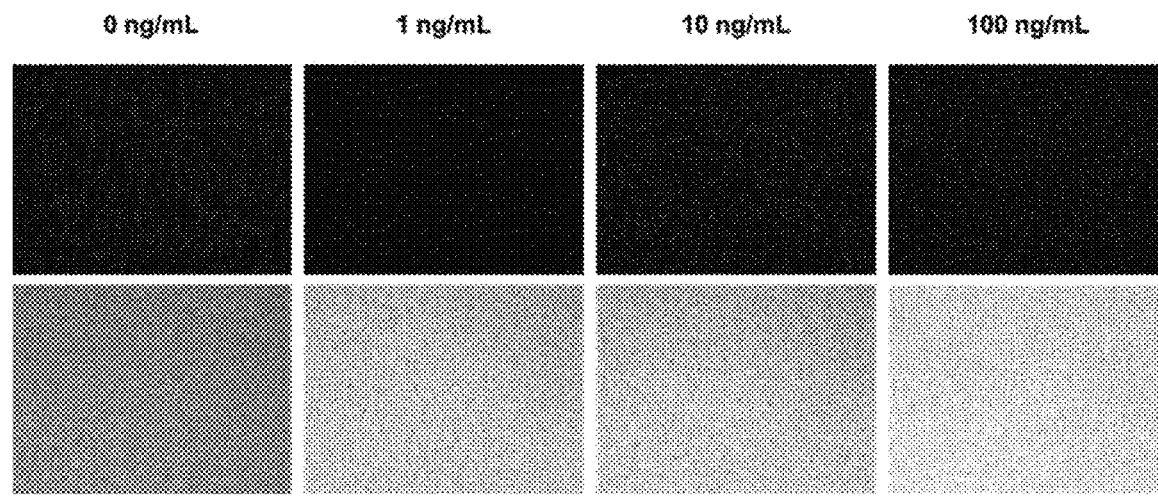
FIG. 7 is a diagram showing change in the number of migrated cells based on increase in a MCP-1 concentration for illustrating Experimental Example 4 of the present disclosure, wherein an upper black image represents a retroreflective image, and a lower bright image represents a bright field image.

Referring to FIG. 7, the retroreflective signals which appear as bright dots due to the retroreflective particles trapped inside the cells via phagocytosis were also observed. It may be identified that as the concentration of the MCP-1 increased from 0 to 10, the number of migrated cells increased based on the dots appearing on the image. On the contrary, it may be identified that the number of migrated cells when using 100 ng/ml concentration of MCP-1 is reduced compared to that when using each of 1 and 10 ng/ml concentrations.

Experimental Example 5: Analysis of Correlation Between Actual Number of Cells and Measured Number of Retroreflective Particles Subsequently, the correlation between the number of cells migrating according to the increase of the content of the chemoattractant as counted in the bright field image and the number of retroreflective signals counted in the retroreflective image was analyzed, and the results are as shown in FIG. 8.

Figure 8:
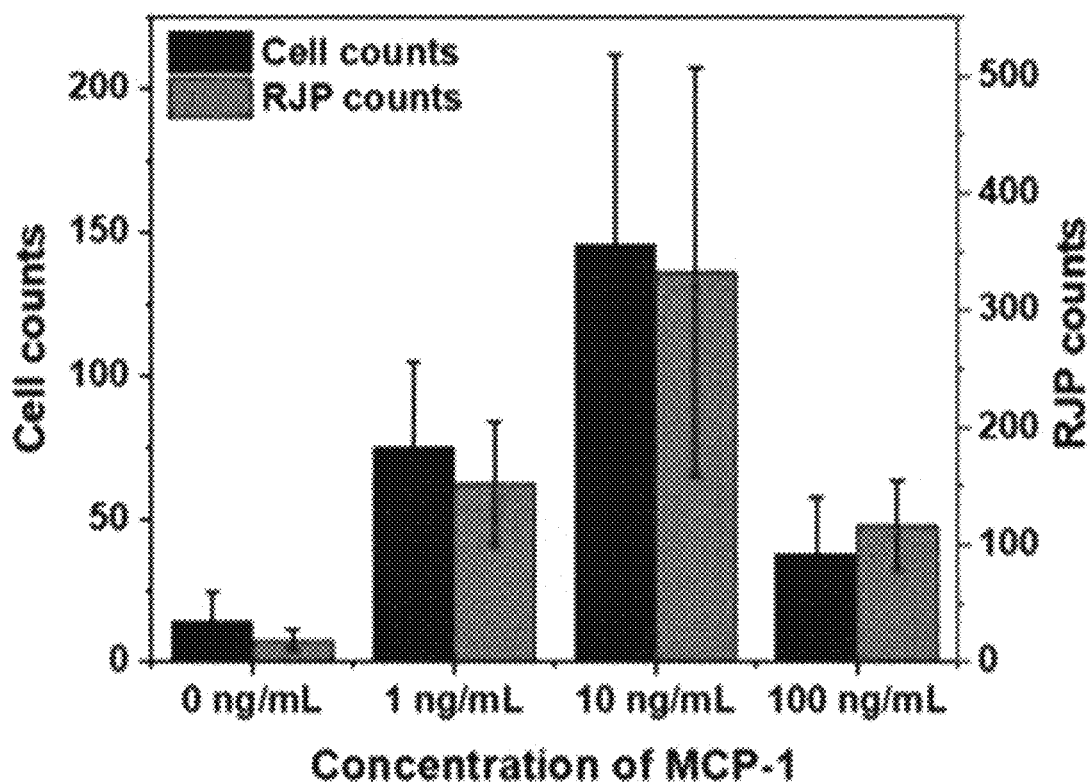
FIG. 8 is a diagram showing a correlation between the actual number of cells and the measured number of RJPs for illustrating Experimental Example 5 of the present disclosure.

Referring to FIG. 8, the number of retroreflective particles as measured was larger by approximately 2.2 times than the number of cells. This indicates that the number of migrated cells may be quantified only based on a measuring result of the number of retroreflective particles compared to that in the control.

Although the present disclosure has been described with reference to preferred embodiments of the present disclosure, it will be appreciated that those skilled in the art may variously modify and change the present disclosure within the scope not departing from the spirit and scope of the present disclosure as described in the claims below.

What is claimed is:

1. An optical sensor comprising:
   a first chamber having a first inner space receiving therein cells and a first culture medium;
   a second chamber having a second inner space receiving therein a second culture medium and a chemoattractant, wherein the chemoattractant activates migration ability of the cells, wherein the second chamber is coupled to the first chamber so that a bottom of the first chamber is immersed in the second culture medium;
   a light-emitter for irradiating light into an inside of the second chamber; and
   a light-receiver configured to generate an optical image of light retroreflected from the inside of the second chamber, and to perform quantitative analysis of the retroreflected light based on the optical image,
   wherein the first chamber includes:
      the bottom having pores defined therein through which the cells can migrate into the second chamber; and
      a coating layer disposed on the bottom, wherein the coating layer contains retroreflective particles therein, each having a size smaller than a size of each of the pores, wherein the retroreflective particles are capable of retroreflecting the light therefrom.

2. The optical sensor of claim 1, wherein the cells inside the first chamber migrate through the coating layer, and migrate into the second chamber in a state in which the cells contain therein the retroreflective particles or in a state in which the retroreflective particles bind to the cells.

3. The optical sensor of claim 1, wherein the coating layer includes:
   a matrix made of a biocompatible material-containing gel; and
   the retroreflective particles dispersed in the matrix.

4. The optical sensor of claim 3, wherein the biocompatible material includes one selected from a group consisting of type I collagen, type II collagen, type III collagen, type IV collagen, polycaprolactone, gelatin, poly(lactic-co-glycolic acid), hyaluronic acid, and extracellular matrix (ECM).

5. The optical sensor of claim 3, wherein the coating layer includes:
   a permeable area thorough which the cells can migrate; and
   a blocking area located adjacent to the permeable area, wherein the blocking area blocks the cell migration,
   wherein the permeable area includes a first matrix made of a gel containing the biocompatible material at a first concentration, and the retroreflective particles dispersed in the first matrix,
   wherein the blocking area includes a second matrix made of a gel containing the biocompatible material at a second concentration higher than the first concentration.

6. The optical sensor of claim 1, wherein the light-emitter irradiates the light through a bottom of the second chamber into the inside of the second chamber,
   wherein the bottom of the second chamber is made of a transparent polymer material.

7. The optical sensor of claim 6, wherein the bottom of the second chamber is made of one selected from a group consisting of PMMA (Poly(methyl methacrylate)), PC (polycarbonate), and PS (polystyrene).

8. The optical sensor of claim 1, wherein the light-receiver is configured to receive the retroreflected light, and to determine change in the number of the retroreflective particles in real time and to analyze the migration of the cells in real time based on the change.

9. A cell mobility analysis method comprising:
   a first step including:
      injecting cells and a first culture medium into a first inner space of a first chamber, wherein the first chamber includes a bottom having pores defined therethrough, and a coating layer disposed on the bottom, wherein the coating layer contains retroreflective particles therein, each having a size smaller than a size of each of the pores, wherein the retroreflective particles are capable of retroreflecting light therefrom; and
      injecting a chemoattractant and a second culture medium into a second inner space of the second chamber receiving therein the bottom of the first chamber;
   a second step of irradiating light into an inside of the second chamber; and
   a third step of generating and analyzing an optical image of light retroreflected from the inside of the second chamber,
   wherein the chemoattractant is diffused into the first inner space to activate the cells to migrate through the coating layer such that the cells migrate from the first inner space to the inside of the second chamber in a state in which the cells contain therein the retroreflective particles or in a state in which the retroreflective particles bind to the cells,
   wherein the third step is performed using the light retroreflected from the retroreflective particles in the second inner space.

10. The cell mobility analysis method of claim 9, wherein while the cells migrate through the coating layer, the cells capture therein the retroreflective particles via uptake or phagocytosis of the cells or the cells bind to a first bio-cognitive material on a surface of the retroreflective particle,
  wherein the cells migrate into the inside of the second chamber in a state in which the cells capture therein the retroreflective particles or in a state in which the cells bind to the first bio-cognitive material on the surface of the retroreflective particle.

11. The cell mobility analysis method of claim 9, wherein the migration of the cells is performed at a temperature of 35 to 38° C. and under a 3 to 7% carbon dioxide condition.

12. The cell mobility analysis method of claim 9, wherein in the third step, the migration of the cells is analyzed in real time, based on change in the number of the retroreflective particles in real time.

13. The cell mobility analysis method of claim 9, wherein in the third step, the cell migration is quantitatively analyzed based on a counting result of a number of retroreflective signals from the generated image.

\* \* \* \* \*